United States Patent [19]

Wilson et al.

[11] 4,420,085
[45] Dec. 13, 1983

[54] STAND UP ORGANIZER

[75] Inventors: Earl D. Wilson, Ingleside; Martin J. Holmes, Chicago, both of Ill.

[73] Assignee: The Kendall Company, Boston, Mass.

[21] Appl. No.: 339,537

[22] Filed: Jan. 15, 1982

[51] Int. Cl.³ .................. B65D 69/00; B65D 71/00
[52] U.S. Cl. ............................ 206/571; 206/560; 206/564; 206/370
[58] Field of Search .............. 206/63.3, 370, 571, 206/570, 234, 560, 562, 563, 564

[56] References Cited

U.S. PATENT DOCUMENTS 2,313,905  3/1943  Wallin ........................... 206/571
3,013,656  12/1961  Murphy, Jr. .................. 206/571

Primary Examiner—Joseph Man-Fu Moy
Attorney, Agent, or Firm—Powell L. Sprunger

[57] ABSTRACT

An organizer for a medical procedure comprising, a syringe having a hollow barrel, and an elongated cap releasably attached to a distal portion of the syringe. The organizer has a tray having an upper wall, and a syringe recess in the upper wall shaped to releasably receive a distal end of the cap with the syringe in an upright position.

5 Claims, 10 Drawing Figures

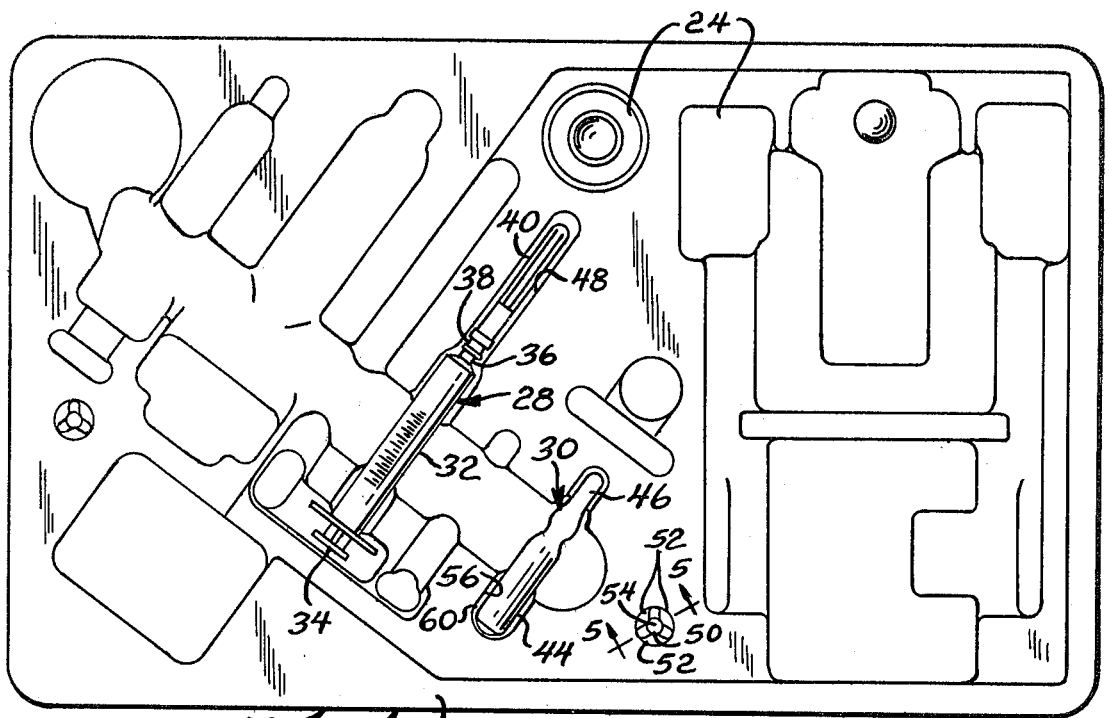
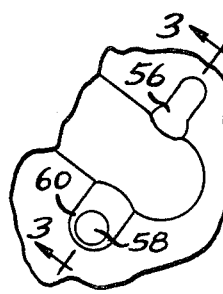
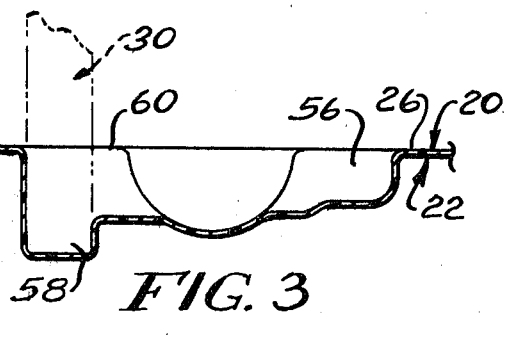
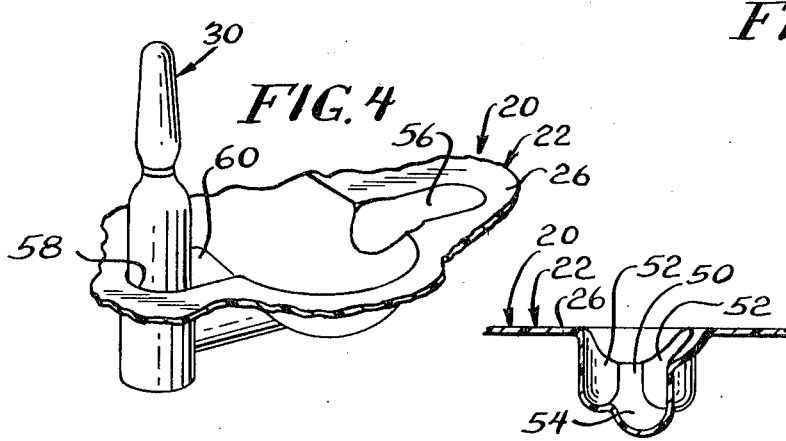
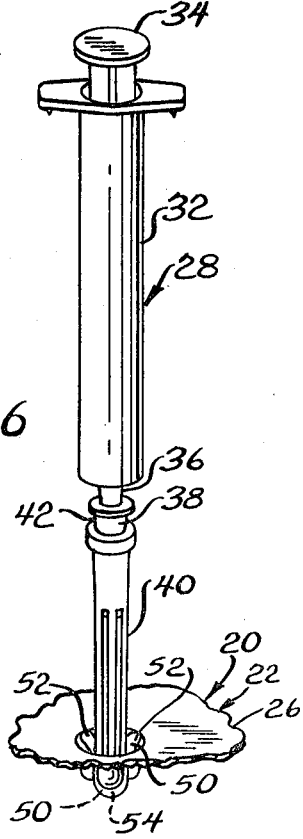

STAND UP ORGANIZER

BACKGROUND OF THE INVENTION

The present invention relates to organizers for medical procedures.

In the past, an assortment of trays have been utilized to hold a number of sterile components for use during a medical procedure, such as an anesthesia procedure. However, during the procedure the various components become strewn throughout a working surface for the physician, thus making it more difficult to locate a desired component, and unnecessarily complicating the procedure by the spread out components. In addition, the components have required an unduly large working space which is at a premium in the operating room. Also, prior trays enhance the possibility that a component might become contaminated on the working surface.

SUMMARY OF THE INVENTION

A principal feature of the present invention is the provision of an organizer for a medical procedure.

The organizer of the invention comprises, a syringe having a hollow barrel, and an elongated cap releasably attached to a distal portion of the syringe. The organizer has a tray having an upper wall, with the upper wall having an elongated groove to receive the syringe in a lay-flat configuration. The upper wall has a syringe recess shaped to releasably receive a distal end of the cap. The organizer may have an ampoule having a hollow body portion, and the upper wall of the tray may have an elongated groove to receive the ampoule in a lay-flat condition. The upper wall of the tray may have an ampoule recess adjacent an end of the groove for the ampoule.

A feature of the present invention is that the syringe recess retains the syringe in an upright position.

Another feature of the invention is that the syringe may be removed from the cap for use of the syringe during the medical procedure, after which the syringe may be placed back into the cap.

Thus, another feature of the invention is that the tray retains the syringe in a convenient position for use during the medical procedure.

Yet another feature of the invention is that the top of the ampoule may be broken, and the body portion of the ampoule may be placed in the ampoule recess to retain the ampoule in an upright position.

Thus, a feature of the present invention is that the tray retains the ampoule in a convenient configuration for use during the medical procedure.

A further feature of the invention is that the syringe may be utilized to remove liquid contents from the ampoule.

Still another feature of the invention is that the syringe recess may be placed adjacent an end of the ampoule groove, such that the syringe is in a convenient position for use with the ampoule.

Yet another feature of the invention is that the tray organizes the components for convenient use during the medical procedure.

A further feature of the invention is that the tray may have a metal base to prevent tipping of the tray during use.

Further features will become more fully apparent in the following description of the embodiments of this invention and from the appended claims.

DESCRIPTION OF THE DRAWINGS

In the drawings:

FIG. 1 is a top plan view of an organizer tray which illustrates the tray components of a syringe and an ampoule;

FIG. 2 is a fragmentary plan view illustrating an ampoule groove in an upper wall of the tray with the ampoule removed;

FIG. 3 is a fragmentary sectional view taken substantially as indicated along the line 3—3 of FIG. 2;

FIG. 4 is a fragmentary perspective view illustrating the retention of the ampoule in an upright position in a recess of the tray upper wall;

FIG. 5 is a fragmentary sectional view of a syringe recess taken substantially as indicated along the line 5—5 of FIG. 1;

FIG. 6 is a fragmentary perspective view illustrating the use of the syringe recess to place the syringe in an upright position in the tray;

DESCRIPTION OF THE PREFERRED EMBODIMENTS

Figure 7:
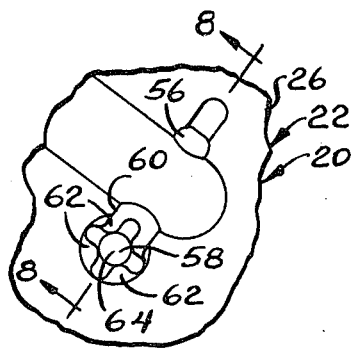
FIG. 7 is a fragmentary plan view of another embodiment of the present invention.

Referring now to FIGS. 1-6, there is shown a stand up organizer generally designated 20 comprising a tray 22 of suitable plastic material having a plurality of recesses 24 in an upper wall 26 of the tray 22 to receive a plurality of components, such as a syringe 28 and an ampoule 30. The syringe 28 may be of the type having an elongated hollow barrel 32, a plunger 34 slidably received in the barrel 32, a tip 36 extending distally from the barrel 32, and a hub 38 attached to the tip 36, with the hub 38 having an elongated distally extending needle (not shown). As shown, an elongated hollow cap 40 is releasably attached to the hub 38 at a distal portion 42 of the syringe 28 in order to receive and cover the syringe needle. The ampoule 30 has a cylindrical hollow body portion 44 to retain liquid contents in the ampoule 30, and a top 46 which is broken from the ampoule 30 in order to expose the liquid contents during use of the tray 22.

The upper wall 26 of the tray 22 has an elongated groove 48 to receive the syringe 28 in a lay-flat configuration in the tray 22 prior to use of the tray 22. Also, the tray 22 has a syringe recess 50 having a plurality of bosses 52, such as three, defining a central opening 54 to receive a distal end of the syringe cap 40. Thus, the syringe 28 may be removed from the groove 48, and, as shown in FIG. 6, the distal end of the cap 40 may be positioned in the opening 54, such that the bosses 52 frictionally engage the distal end of the cap 40 and retain the syringe 28 in an upright position in the tray 22. In this configuration, the syringe 28 may be removed from the cap 40 in order to expose the needle of the syringe 28, and, after use of the syringe 28, the syringe 28 may be reinserted into the cap 40 in order to retain the syringe 28 again in an upright position.

As shown, the upper wall 26 of the tray 22 also has an elongated groove 56 to receive the ampoule 30 in a lay-flat configuration prior to use of the tray 22. The upper wall 26 of the tray 22 has a generally cylindrical ampoule recess 58 adjacent one end 60 of the groove 56 to snugly receive the lower part of the ampoule body portion 44. Thus, as shown in FIG. 4, the ampoule 30 may be removed from the groove 56, and the body portion 44 of the ampoule 30 may be placed in the recess 58 in order to retain the ampoule 30 in an upright configuration. Of course, the top 46 of the ampoule 30 may be broken prior to placing the ampoule 30 in the upright position in order to expose the liquid contents in the ampoule 30.

Thus, in accordance with the present invention, the syringe 28 may be placed in an upright position in the recess 50, and the ampoule 30 may be placed in an upright position in the recess 58. The syringe 28 may be removed from the cap 40, and the needle of the syringe 28 may be placed through the broken top of the ampoule 30 in order to remove the liquid contents from the ampoule 30 through manipulation of the syringe 28. After use of the syringe 28 in the medical procedure, during which the liquid contents of the ampoule 30 are injected by the syringe into the patient, the syringe 28 may be again placed in th cap 40 in order to retain the syringe 28 in an upright position. Thus, the tray 22 of the invention minimizes the amount of space that is required for the medical procedure, and organizes the components for use in a convenient manner in order to simplify the procedure.

Figure 8:
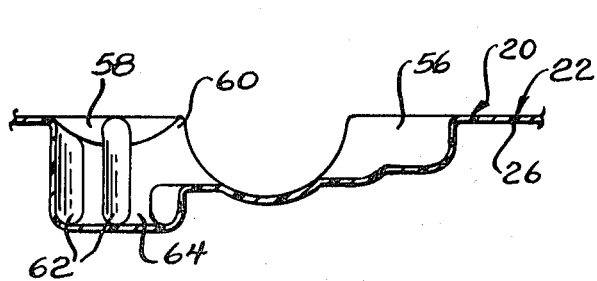
FIG. 8 is a fragmentary sectional view taken subtantially as indicated along the line 8—8 of FIG. 7.

Another embodiment of the present invention is illustrated in FIGS. 7 and 8, in which like reference numerals designate like parts. In this embodiment, the upper wall 26 of the tray 22 also has an ampoule recess 58 adjacent the one end 60 of the groove 56. However, in this embodiment, the recess 58 has a plurality of bosses 62 defining a central opening 64 to receive the lower part of the ampoule with the ampoule in an upright position. In this embodiment, the bosses 62 frictionally engage against the body portion of the ampoule in order to retain the ampoule 30 in the upright position.

Figure 9:
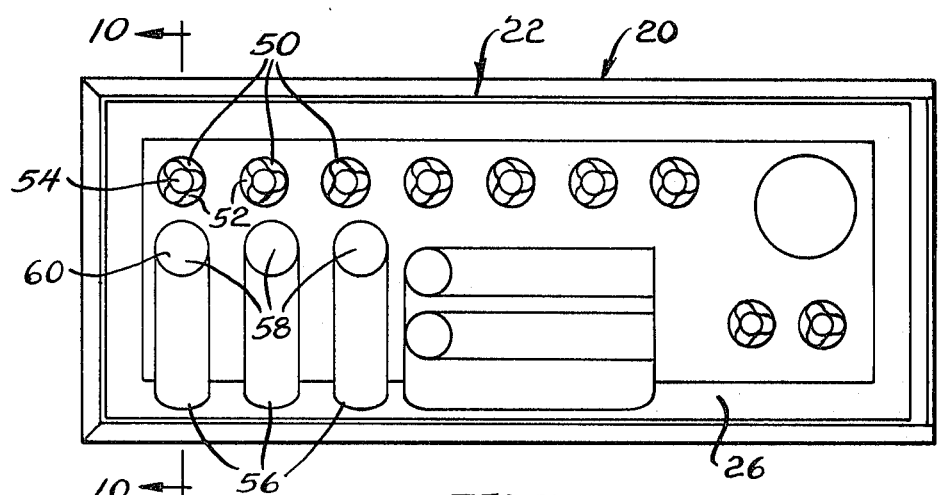
FIG. 9 is a top plan view of another embodiment of the organizer of the present invention.
Figure 10:
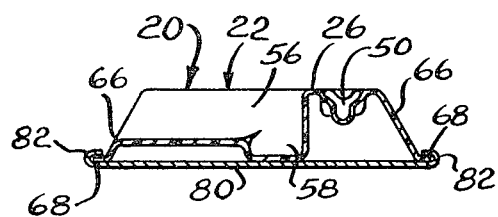
FIG. 10 is a sectional view taken substantially as indicated along the line 10—10 of FIG. 9.

Another embodiment of the present invention is illustrated in FIGS. 9 and 10, in which like reference numerals designate like parts. In this embodiment, the tray 22 has a plurality of grooves 56 to retain ampoules in a lay-flat condition, and associated recesses 58 at one end 60 of the grooves 56 to retain the ampoules in an upright position. In this embodiment, the tray 22 has a plurality of syringe recesses 50 to receive the cap associated with the syringe, and retain the syringes in an upright position. As shown, the syringe recesses 50 may be located adjacent the recesses 58 for the ampoules in order to organize one syringe in an upright position for use with each associated ampoule which is in the grooves 56 aligned with the recesses 50.

Also, in this embodiment, the tray 22 has a pair of sidewalls 66 extending downwardly from opposed sides of the tray upper wall 26. The sidewalls 66 have an outwardly directed flange 68 at a lower end of the sidewalls 66. The tray 22 has a base 80 of relatively heavy material, such as a suitable metal, with the base 80 having a pair of opposed C-shaped flanges 82 to receive the flanges 68. In this configuration, the base 80 is attached to a lower portion of the tray 22, and the relatively heavy base 80 prevents tipping of the tray 22 during use.

The foregoing detailed description is given for clearness of understanding only, and no unnecessary limitations should be understood therefrom, as modification will be obvious to those skilled in the art.

We claim:

1. An organizer for a medical procedure, comprising:
a syringe having a hollow barrel;
an elongated cap releasably attached to a distal portion of the syringe;
a tray having an upper wall, and a syringe recess in said upper wall shaped to frictionally engage and releasably secure a distal end of said cap with the syringe in an upright position, said syringe recess further comprising means defining a plurality of bosses therein, the said bosses frictionally engaging and releasably securing the distal end of said cap therewithin;
an elongated groove defined in the upper wall of said tray for receiving the syringe in a lay-flat condition;
an ampoule having a hollow body portion and a top which may be broken from the body;
an additional, elongated groove defined in the upper wall of said tray for receiving the ampoule in a lay-flat condition; and
an ampoule recess defined in an end of said additional, elongated groove for receiving the body portion of the ampoule with the ampoule in an upright position;
whereby, during a medical procedure, the ampoule top is broken from the ampoule to provide access to liquid contents in the ampoule body portion, the ampoule is placed upright in the ampoule recess, the syringe is placed in an upright position with the distal end of the cap inserted in the syringe recess between the bosses therein, the syringe is removed from the cap, the cap being retained by the bosses of the syringe recess, the syringe is manipulated to withdraw liquid contents from the ampoule hollow body, and, after use of the syringe in a medical procedure, the syringe is again placed in the cap, in an upright position.

2. The organizer of claim 1 wherein the ampoule recess further comprises means defining a plurality of bosses therein, the said ampoule bosses frictionally engaging and releasably securing the body portion of the ampoule therewithin, with the ampoule in an upright position.

3. The organizer of claim 1 wherein the syringe recess is located adjacent an end of the groove.

4. The organizer of claim 3 wherein the syringe recess is located adjacent said ampoule recess.

5. The organizer of claim 1 wherein the ampoule body portion and the ampoule recess are generally cylindrical.

* * * * *